(12) United States Patent
Schattenmann et al.

(10) Patent No.: US 6,399,790 B1
(45) Date of Patent: Jun. 4, 2002

(54) METHOD FOR OXIDATION OF XYLENE DERIVATIVES

(75) Inventors: Sheree Lynell Schattenmann, Ballston Lake; Bahram Moasser, Schenectady; Joseph John Caringi, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/718,124

(22) Filed: Nov. 20, 2000

Related U.S. Application Data

(60) Provisional application No. 60/167,266, filed on Nov. 24, 1999.

(51) Int. Cl.⁷ .................. C07C 51/23; C07C 51/215; C07D 307/89
(52) U.S. Cl. .................. 549/307; 562/485; 562/494
(58) Field of Search .................. 549/307; 562/485, 562/494

(56) References Cited

U.S. PATENT DOCUMENTS

| | | |
|---|---|---|
| 3,402,184 A | 9/1968 | Bethoux et al. |
| 4,215,053 A | 7/1980 | Palmer et al. |
| 4,299,977 A | 11/1981 | Kuhlmann et al. |
| 4,322,549 A | 3/1982 | Kuhlmann et al. |
| 4,387,243 A | 6/1983 | Naim et al. |
| 4,436,922 A | 3/1984 | Kita et al. |
| 4,992,580 A | 2/1991 | Partenheimer |
| 5,112,992 A | 5/1992 | Belmonte et al. |
| 5,225,573 A | 7/1993 | Shorr et al. |
| 5,229,482 A | 7/1993 | Brunelle |
| 5,322,954 A | 6/1994 | Seper et al. |
| 5,359,133 A | 10/1994 | Nazimok et al. |
| 5,830,974 A | 11/1998 | Schmidhauser et al. |
| 5,958,821 A | 9/1999 | Ishii et al. |
| 5,981,420 A | 11/1999 | Nakano et al. |
| 6,020,522 A | 2/2000 | Ishii et al. |

OTHER PUBLICATIONS

PCT Search Report, PCT/US 00/31971.
*Liquid–Phase Catalytic Oxidation of 4–Bromo–o–Xylene*, 6001 Chemical Abstracts, Columbus, Ohio, US vol. 90, 38640, No. 5, G. Uzulneice et al., Latv. PSR Zinat. Akad, Vestis, Kim. Ser. 1978, vol. 5, pp. 617–620,.
*Preparation of Monochlorophthalic Acids By the Liquid–Phase Catalytic Oxidation of Chloro–o–Xylenes*, , 6001 Chemical Abstracts, Columbus, Ohio, US vol. 101, 230079, No. 25, ES Nazarenko et al., UKr. Him. Zh. 1984, vol. 50(6), pp. 644–647.

*Primary Examiner*—T. A. Solola
(74) *Attorney, Agent, or Firm*—S. Bruce Brown; Noreen C. Johnson

(57) ABSTRACT

Xylene derivatives, such as chloro-ortho-xylene, are oxidized in a solvent in the presence of at least one metal catalyst and optionally at least one promoter. The product comprises chlorophthalic acid or chlorophthalic anhydride.

22 Claims, No Drawings

METHOD FOR OXIDATION OF XYLENE DERIVATIVES

This application claims priority of a Provisional Application, Serial No. 60/167,266, filed Nov. 24, 1999.

BACKGROUND OF THE INVENTION

This invention relates to a method for oxidizing xylene derivatives. More particularly, the invention relates to a method for oxidizing a substrate comprising at least one halo-ortho-xylene in the presence of at least one metal catalyst, at least one solvent, and optionally at least one promoter to provide a product comprising halo-phthalic acid or halo-phthalic anhydride. In one key embodiment the invention relates to a method for producing a product comprising 4-chlorophthalic acid or 4-chlorophthalic anhydride.

Methods for oxidizing ortho-xylene are known. For example, U.S. Pat. No. 3,402,184 describes oxidation of ortho-xylene in acetic acid solvent in the presence of a bromine promoter. U.S. Pat. Nos. 5,958,821, 5,981,420, and 6,020,522 describe oxidation of ortho-xylene in acetic acid solvent in the presence of a hydroxyimide promoter. Methods for preparing 4-chlorophthalic anhydride are also known. However, these methods typically involve aromatization of a Diels-Alder adduct of chloroprene and a maleic anhydride as in U.S. Pat. No. 5,322,954, or chlorination of phthalic acid as in Japanese patent applications 07258152 and 02129143. The latter chlorination process may produce polychlorinated biphenyls (PCBs). There is a need for a method for producing 4-chlorophthalic anhydride which does not involve handling toxic chloroprene or chlorine gas, and which does not produce PCBs.

SUMMARY OF THE INVENTION

In one embodiment the invention is a method for oxidizing a substrate comprising at least one halo-ortho-xylene which comprises combining the substrate in a solvent with at least one metal catalyst and heating in the presence of an oxygen source to produce a product mixture.

In another embodiment the invention is a method for oxidizing a substrate comprising 4-chloro-ortho-xylene which comprises combining chloro-ortho-xylene in acetic acid solvent with at least one metal catalyst which is a metal compound comprising cobalt, and heating in the presence of an oxygen source to produce a product mixture comprising 4-chlorophthalic acid or 4-chlorophthalic anhydride.

In still another embodiment the invention is a method for producing a product mixture comprising 4-chlorophthalic acid or 4-chlorophthalic anhydride which comprises oxidizing a substrate comprising 4-chloro-ortho-xylene, optionally in the presence of chlorotoluic acid, which comprises the steps of (i) combining substrate in acetic acid solvent with at least one metal catalyst comprising cobalt, and optionally manganese, and heating in the presence of an oxygen source to a temperature in a range of between about 100° C. and about 230° C. at pressure in a range of between about 1300 and about 8300 kilopascals, wherein the molar ratio of substrate to the at least one metal catalyst is in a range of about 80–250:1; and (ii) isolating product comprising 4-chlorophthalic acid or 4-chlorophthalic anhydride.

DETAILED DESCRIPTION; PREFERRED EMBODIMENTS

In one embodiment the substrate comprising at least one halo-ortho-xylene of the present invention preferably comprises a monohalo-ortho-xylene, more preferably 4-halo-ortho-xylene, most preferably 4-fluoro- or 4-chloro-ortho-xylene. In another embodiment the substrate comprises a mixture of 4-halo- and 3-halo-ortho-xylene, preferably a mixture of 4-fluoro- and 3-fluoro-ortho-xylene or a mixture of 4-chloro- and 3-chloro-ortho-xylene. When 3-halo-ortho-xylene is present, it comprises about 0.001–15 molar percent, preferably about 0.01–12 molar percent, and more preferably about 0.1–10 molar percent of total substrate.

In yet another embodiment the substrate comprises at least one halo-ortho-xylene as described above, optionally in the presence of at least one halotoluic acid, preferably at least one chlorotoluic acid (also known as chloro methylbenzoic acid), more preferably either (a) 4-chloro-2-methyl benzoic acid or (b) 5-chloro-2-methylbenzoic acid or (c) a mixture thereof, and still more preferably a mixture of either or both of (a) and (b) with either (d) 4-halo-ortho-xylene, or (e) a mixture of 4-halo- and 3-halo-ortho-xylene. Halotoluic acid may be either added to the substrate or may be present as a consequence of partial oxidation of halo-ortho-xylene. As a consequence of partial oxidation the amount of halo-toluic acid in the substrate will vary with such factors as reaction temperature, time, and catalyst.

In still another embodiment the substrate comprises a mixture of ortho-xylene with halo-ortho-xylene, preferably either with (d) 4-halo-ortho-xylene, or with (e) a mixture of 4-halo- and 3-halo-ortho-xylene, or with at least one halotoluic acid, preferably chlorotoluic acid, or with a mixture of chlorotoluic acid with either (d) 4-halo-ortho-xylene, or (e) a mixture of 4-halo- and 3-halo-ortho-xylene. When ortho-xylene is present, it comprises about 0.001–10 molar percent and preferably about 0.01–1 molar percent of total substrate. An especially preferred substrate comprises 4-chloro-ortho-xylene, optionally in combination with at least one of 3-chloro-ortho-xylene, ortho-xylene, or chlorotoluic acid.

The substrate comprising at least one halo-ortho-xylene is combined in the reaction mixture with at least one solvent, which preferably comprises a lower aliphatic carboxylic acid. Illustrative examples of lower aliphatic carboxylic acids employed in the process of the present invention, include, but are not limited to, acetic acid, propionic acid, butanoic acid, pentanoic acid, or hexanoic acid. Acetic acid is preferred.

At least one metal catalyst is used in the present invention. The at least one metal catalyst comprises a metal compound with a metal selected from the group consisting of cobalt, manganese, vanadium, copper, molybdenum, and iron, and mixtures thereof. Preferably, a metal compound is a salt of the metal and more preferably an acetate or acetylacetonate of the metal. Illustrative metal compounds which are suitable for use in the invention include, but are not limited to, cobalt dibromide hexahydrate, cobalt dichloride, cobalt (II) acetate, cobalt (II) acetylacetonate, cobalt (III) acetylacetonate, cobalt (II) hexafluoroacetylacetonate, cobalt (II) picolinate, manganese (III) acetate, manganese (II) acetate, manganese (II) hexafluoroacetylacetonate trihydrate, manganese (III) acetylacetonate, manganese (II) acetylacetonate, manganese dichloride tetrahydrate, manganese dibromide, manganese (II) picolinate, manganese (III) picolinate, manganese (III) bromide acetylacetonate, vanadyl (IV) acetate (VO[OC(O)CH$_3$]$_2$), vanadyl (IV) acetylacetonate, copper (I) acetate, molybdenyl (VI) acetylacetonate (MoO$_2$[C$_5$H$_7$O$_2$]), iron (II) acetate, and hydrates, and anhydrous compounds, and mixtures thereof. Preferred metal catalysts include mixtures of cobalt (II) bromide hexahydrate with either cobalt (II) picolinate, manganese (II) bromide, manganese (II) chloride tetrahydrate, manganese (III) bromide acetylacetonate, manganese (II) acetate, manganese (III) acetate dihydrate, manganese (II) acetylacetonate, manganese (III) acetylacetonate, or manganese (II) hexafluoroacetylacetonate trihydrate; mixtures of cobalt (II) acetate with manganese (III) acetate or manganese (II) bromide; and ternary mixtures of cobalt (II) acetate with manganese (III) acetate and manganese (II) bromide; or of cobalt (II) acetate with manganese (III) acetate and cobalt (II) bromide; or of cobalt (II) acetate with manganese (III) acetate and iron (II) bromide; or of cobalt (II) acetate with manganese (III) acetate and either copper (I) bromide or copper (II) bromide.

The molar ratio of halo-ortho-xylene substrate to the at least one metal catalyst is in a range of about 20–600:1, preferably in a range of about 50–300:1, and most preferably in a range of about 80–250:1. In especially preferred embodiments the molar ratio of halo-ortho-xylene substrate to the at least one metal catalyst is about 200:1. The at least one metal catalyst may be added in one portion to the substrate or in more than one portion during the course of the reaction.

An effective amount of at least one promoter may optionally be used in the reaction mixture. The term "effective amount", as used herein, includes that amount of promoter capable of either increasing (directly or indirectly) the conversion of halo-ortho-xylene or increasing selectivity toward halo-phthalic acid or halo-phthalic anhydride. Optimum amounts of promoter can vary based on reaction conditions and the identity of other constituents, yet can be readily determined in light of the discrete circumstances of a given application. In typical embodiments an effective amount of promoter may have a value in a range between about 0.01 mole % and about 20 mole %, preferably between about 0.1 mole % and about 12 mole %, and more preferably between about 0.4 mole % and about 10 mole %, based on halo-ortho-xylene substrate.

Suitable organic promoters include, but are not limited to,
(i) imides such as phthalimide, 4-chloro-phthalimide, 3-chloro-phthalimide, dichloro-phthalimide, N-hydroxyethylphthalimide, and N-hydroxymethylphthalimide;
(ii) N-hydroxy imides such as N-hydroxyphthalimide, 4-chloro-N-hydroxyphthalimide, 3-chloro-N-hydroxyphthalimide, dichloro-N-hydroxyphthalimide, 4-bromo-N-hydroxyphthalimide, 3-bromo-N-hydroxyphthalimide, dibromo-N-hydroxyphthalimide, N-hydroxymaleimide, and N-hydroxysuccinimide;
(iii) hydroxamic acids such as 2-carboxyethanehydroxamic acid, 2-carboxyethenehydroxamic acid, and 2-carboxyphenylhydroxamic acids of formula I:

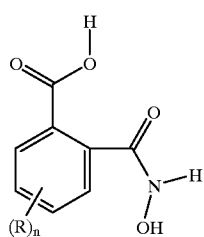

(I)

wherein each R is independently halogen, preferably chloro or bromo; or alkyl, and n is 0–4;
(iv) arylaldehydes such as substituted benzaldehydes of the formula (II):

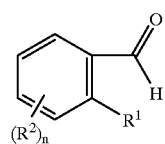

(II)

wherein $R^1$ is alkyl and each $R^2$ is independently halogen, preferably chloro or bromo; or alkyl, and n is 0–4;
(v) onium halides such as ammonium halides and phosphonium halides, preferably chlorides or bromides;
(vi) guanidinium halides, preferably chlorides or bromides; and
(vii) alkali metal halides, preferably chlorides or bromides.

Preferred hydroxamic acids include, but are not limited to, unsubstituted 2-carboxyphenylhydroxamic acid, 4-chloro-2-carboxyphenylhydroxamic acid, 3-chloro-2-carboxyphenylhydroxamic acids, and dichloro-2-carboxyphenylhydroxamic acid. Preferred arylaldehydes include, but are not limited to, alkylchlorobenzaldehydes such as 3-chloro-2-methylbenzaldehyde, 4-chloro-2-methylbenzaldehyde, and dichloro-2-methylbenzaldehyde. Preferred onium halides include, but are not limited to, tetraalkylammonium bromides such as tetraethylammonium bromide and tetrabutylammonium bromide. Preferred guanidinium halides are hexaethylguanidinium chloride and hexaethylguanidinium bromide. A preferred alkali metal halide is sodium bromide. Especially preferred promoters are N-hydroxyphthalimide and 4-chloro-N-hydroxyphthalimide.

The term "alkyl" as used in the various embodiments of the present invention is intended to designate both normal alkyl, branched alkyl, aralkyl, and cycloalkyl radicals. Normal and branched alkyl radicals are preferably those containing from 1 to about 12 carbon atoms, and include as illustrative non-limiting examples methyl, ethyl, propyl, isopropyl, butyl, tertiary-butyl, pentyl, neopentyl, and hexyl. Cycloalkyl radicals represented are preferably those containing from 3 to about 12 ring carbon atoms. Some illustrative non-limiting examples of these cycloalkyl radicals include cyclobutyl, cyclopentyl, cyclohexyl, methylcyclohexyl, and cycloheptyl. Preferred aralkyl radicals are those containing from 7 to about 14 carbon atoms; these include, but are not limited to, benzyl, phenylbutyl, phenylpropyl, and phenylethyl.

The oxygen source used in the present invention may be high purity oxygen or molecular oxygen, air, oxygen-enriched air, or oxygen diluted with another gas which has no negative effects on the reaction, such as nitrogen, noble gases, argon. The concentration of diluent gas, when present, in the oxygen source may amount to about 1 to about 95 volume %, preferably about 5 to about 90 volume %, and more preferably about 10 to about 80 volume %. In a preferred embodiment the oxygen source is oxygen-enriched air containing about 28 mole % oxygen.

Oxygen in the form of an oxygen source may be introduced into the reaction mixture by any convenient means. In one embodiment the reaction mixture is agitated or stirred under a positive pressure of oxygen source. A preferred pressure is in a range of between about 1300 and about 8300 kilopascals. A more preferred pressure is in a range of between about 3400 and about 7100 kilopascals. In an especially preferred embodiment the pressure is about 6900 kilopascals.

The reaction mixture is heated to a temperature effective to promote oxidation of at least one of and preferably both methyl groups of halo-ortho-xylene in the presence of the at least one catalyst and oxygen source. Preferably the reaction mixture is heated to a temperature in a range of between about 80° C. and either the temperature at which either catalyst or promoter is no longer effective for promoting reaction or the effective boiling point of the reaction mixture under the prevailing pressure, whichever of the two is the lower temperature. More preferably the reaction mixture is heated to a temperature in a range of between about 100° C. and about 230° C. and most preferably in a range of between about 110° C. and about 150° C. at the prevailing pressure.

The products of the oxidation reaction comprise those obtained by oxidation of at least one of and preferably both the two aromatic methyl groups. In particular the products comprise halotoluic acid and halophthalic acid, respectively. Halophthalic anhydride may also be present depending upon the reaction conditions. It is to be understood that product mixtures comprising halophthalic acid may comprise up to 100% halophthalic anhydride assuming all the halophthalic acid has dehydrated. In a preferred embodiment the substrate halo-ortho-xylene comprises 4-chloro-ortho-xylene and the products comprise chlorotoluic acid and 4-chlorophthalic acid, optionally with 4-chlorophthalic anhydride. In another preferred embodiment the substrate chloro-ortho-xylene comprises a mixture of 3-chloro- and 4-chloro-ortho-xylene and the products comprise chlorotoluic acids and a mixture of 3-chloro- and 4-chlorophthalic acid optionally with 3-chloro- and 4-chlorophthalic anhydride. When ortho-xylene is present in the substrate, then a small amount of toluic acid and phthalic acid (optionally with phthalic anhydride) may also be obtained in addition to the oxidation products of halo-ortho-xylene.

The product halophthalic anhydrides (or halophthalic acids which may be converted to halophthalic anhydrides) may be used in processes to make various types of aromatic polyethers, particularly polyetherimides. In one embodiment a product comprising 4-chlorophthalic anhydride (or a mixture thereof with 3-chlorophthalic anhydride) may be reacted with at least one diamine to prepare bis (chlorophthalimide) compounds which can serve as monomer for polyetherimide synthesis. For example, polyetherimides are conveniently prepared by the reaction of salts of dihydroxyaromatic compounds, such as a bisphenol A disodium salt, with bis(halophthalimides) as illustrated by 1,3-bis[N-(4-chlorophthalimido)]benzene, which has the structure

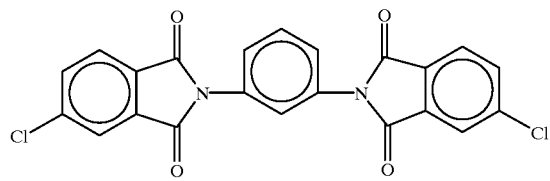

According to U.S. Pat. Nos. 5,229,482 and 5,830,974, the preparation of aromatic polyethers may be conducted in solution in relatively non-polar solvents, using a phase transfer catalyst which is substantially stable under the temperature conditions employed. Solvents disclosed in U.S. Pat. No. 5,229,482 include o-dichlorobenzene, dichlorotoluene, 1,2,4-trichlorobenzene and diphenyl sulfone. In U.S. Pat. No. 5,830,974, monoalkoxybenzenes such as anisole, diphenylether, or phenetole are employed. Solvents of the same types may be used for the preparation of bis(halophthalimide) intermediates, particularly bis(chlorophthalimide) intermediates, for polyetherimides.

The reaction of diamine with 4-halophthalic anhydride (or a mixture thereof with 3-halophthalic anhydride) in the presence of any phthalic anhydride arising from ortho-xylene oxidation may produce trace amounts of the mono-halo species. For example the reaction of diamine with 4-chlorophthalic anhydride (or a mixture thereof with 3-chlorophthalic anhydride) in the presence of any phthalic anhydride arising from ortho-xylene oxidation may produce trace amounts of the mono-halo species, 1-N-(4-chlorophthalimido)-3-N-(phthalimido)benzene in addition to 1,3-bis[N-(4-chlorophthalimido)]benzene (optionally in the presence of 3-chloro species). The mono-halo species may serve as a chain-stopper in reaction with salts of dihydroxyaromatic compounds in polyetherimide synthesis.

The process of the present invention may be performed in batch mode or as a semi-continuous or continuous process. In one embodiment the products of the oxidation reaction may be isolated by conventional means, such as one or more steps of distillation or extraction. In another embodiment the products are at least partially recycled into a further oxidation process to increase conversion of halo-ortho-xylene or to increase conversion of halo-toluic acid, or both.

Embodiments of the invention are illustrated by the following non-limiting examples. When amounts are specified, they apply to the originally incorporated components rather than those remaining after any reaction. Analytical samples were quenched with bis(trimethylsilyl) trifluoroacetamide, diluted with tetrahydrofuran, and analyzed by gas chromatography versus an internal standard. Sample component concentrations, including remaining halo-ortho-xylene starting material, were determined using response factors that were measured using authentic compounds. Although results are reported for chlorophthalic acid, it is to be understood that the sample may have contained at least some chlorophthalic anhydride before quenching and derivatization.

EXAMPLES 1–34

Oxidation reactions were performed at 100° C. and 3447 kilopascals using 28% oxygen-enriched air and 2 molar ortho-chloro-xylene (referred to hereinafter as "4ClOX") in glacial acetic acid in the presence of 0.5 mole % cobalt (II) acetate hexahydrate and 0.5 mole % manganese (III) acetate dihydrate, both based on ortho-chloro-xylene. Different promoters were included in the reaction mixture at either 1 mole % or 10 mole % based on ortho-chloro-xylene. The promoters used were N-hydroxyphthalimide (hereinafter referred to as NHPI), 4-chloro-N-hydroxyphthalimide (4ClNHPI), N-hydroxymaleimide (NHMI), N-hydroxysuccinimide (NHSI), phthalimide (PI), N-hydroxyethylphthalimide (NHEPI), and N-hydroxymethylphthalimide (NHMPI), 2-carboxyphenylhydroxamic acid of formula I (CPHA), and 4-chloro-2-methylbenzaldehyde (4CMB). The reactions were run for 100 minutes before sampling. Duplicate reactions were run in every case. A control reaction run for 60 minutes under the same conditions except without added promoter and using 5 molar concentration of 4ClOX gave no detectable amounts of diacid. Analytical results are shown in Table 1.

TABLE 1

| Example | Promoter (mole %) | 4ClOX Conversion | % Yield Diacid |
|---|---|---|---|
| 1 | NHPI (10) | 100 | 24.6 |
| 2 | NHPI (10) | 100 | 30.9 |
| 3 | 4ClNHPI (10) | 100 | 35.8 |
| 4 | 4ClNHPI (10) | 100 | 35.3 |
| 5 | NHSI (10) | 100 | 40.3 |
| 6 | NHSI (10) | 100 | 41.3 |
| 7 | NHMI (10) | 100 | 5.1 |
| 8 | NHMI (10) | 100 | 5.3 |
| 9 | NHEPI (10) | 89.9 | 4.2 |
| 10 | NHEPI (10) | 90.5 | 4.4 |
| 11 | NHMPI (10) | 91.8 | 5.3 |
| 12 | NHMPI (10) | 96.3 | 8.5 |
| 13 | PI (10) | 98.5 | 9.8 |
| 14 | PI (10) | 96.2 | 7.1 |
| 15 | CPHA (10) | 97.6 | 23.3 |
| 16 | CPHA (10) | 100 | 25.4 |
| 17 | NHPI (1) | 100 | 32.1 |
| 18 | NHPI (1) | 100 | 33.5 |
| 19 | 4ClNHPI (1) | 100 | 32.8 |
| 20 | 4ClNHPI (1) | 100 | 38.8 |
| 21 | NHSI (1) | 100 | 30.5 |
| 22 | NHSI (1) | 100 | 30.4 |
| 23 | NHMI (1) | 97.4 | 14.1 |
| 24 | NHMI (1) | 97.8 | 16.0 |
| 25 | NHEPI (1) | 97.7 | 14.2 |
| 26 | NHEPI (1) | 100 | 15.7 |
| 27 | NHMPI (1) | 100 | 15.3 |
| 28 | NHMPI (1) | 100 | 16.0 |
| 29 | PI (1) | 98.5 | 14.6 |
| 30 | PI (1) | 100 | 15.3 |
| 31 | CPHA (1) | 98.6 | 21.7 |
| 32 | CPHA (1) | 98.0 | 26.6 |
| 33 | 4CMB (1) | 100 | 32.4* |
| 34 | 4CMB (1) | 100 | 38.4* |

*corrected for any product arising from oxidation of promoter

EXAMPLES 35–76

Oxidation reactions were performed at 150° C. and 3447 kilopascals using 28% oxygen-enriched air and 2 molar 4ClOX in glacial acetic acid in the presence of 0.5 mole % cobalt source and 0.5 mole % manganese source, both based on ortho-chloro-xylene. Temperature and pressure were controlled to remain relatively constant throughout the reaction. The promoter NHPI was included in the reaction mixture at 1 mole % based on ortho-chloro-xylene. The reactions were run for 120 minutes before sampling. The catalyst sources used were manganese (III) acetate, manganese (II) acetate, manganese (II) hexafluoroacetylacetonate trihydrate, manganese (III) acetylacetonate, manganese (II) acetylacetonate, manganese dichloride tetrahydrate, manganese dibromide, cobalt dibromide hexahydrate, cobalt dichloride, cobalt (II) acetate, cobalt (II) acetylacetonate, cobalt (III) acetylacetonate, and cobalt (II) hexafluoroacetylacetonate. Duplicate reactions were run in every case. Analytical results are shown in Table 2. The catalyst combinations of manganese (II) acetate with cobalt (II) acetate; cobalt (II) acetylacetonate; cobalt (III) acetylacetonate; and cobalt (II) hexafluoroacetylacetonate gave greater than 80% conversion of 4ClOX in the presence of promoter but no detectable amounts of diacid oxidation products under these conditions.

TABLE 2

| Example | Manganese source | Cobalt source | Promoter mole % | 4ClOX Conversion | % Yield Diacid |
|---|---|---|---|---|---|
| 35 | (acetate)3 | dibromide | none | 100 | 100 |
| 36 | (acetate)3 | dibromide | none | 100 | 100 |
| 37 | (acetate)3 | dibromide | 1 | 100 | 100 |
| 38 | (acetate)3 | dibromide | 1 | 100 | 100 |
| 39 | (acetate)3 | dichloride | none | 65.4 | 0 |
| 40 | (acetate)3 | dichloride | none | 59.9 | 0 |
| 41 | (acetate)3 | dichloride | 1 | 94.3 | 5.2 |
| 42 | (acetate)3 | dichloride | 1 | 100 | 24.1 |
| 43 | (acetate)3 | (acetate)2 | none | 15.1 | 0 |
| 44 | (acetate)3 | (acetate)2 | none | 12.2 | 0 |
| 45 | (acetate)3 | (acetate)2 | 1 | 94.6 | 3.0 |
| 46 | (acetate)3 | (acetate)2 | 1 | 96.8 | 0 |
| 47 | (acetate)3 | (acac)2 | none | 28.9 | 0 |
| 48 | (acetate)3 | (acac)2 | none | 19.6 | 0 |
| 49 | (acetate)3 | (acac)2 | 1 | 94.3 | 5.2 |
| 50 | (acetate)3 | (acac)2 | 1 | 100 | 24.1 |
| 51 | (acetate)3 | (HF-acac)2 | 1 | 83.0 | 0 |
| 52 | (acetate)3 | (HF-acac)2 | 1 | 83.8 | 4.3 |
| 53 | (acetate)2 | dibromide | none | 100 | 100 |
| 54 | (acetate)2 | dibromide | none | 100 | 100 |
| 55 | (acetate)2 | dibromide | 1 | 100 | 100 |
| 56 | (acetate)2 | dibromide | 1 | 100 | 100 |
| 57 | (acetate)2 | dichloride | none | 54.2 | 0 |
| 58 | (acetate)2 | dichloride | none | 56.4 | 0 |
| 59 | (acetate)2 | dichloride | 1 | 95.0 | 12.9 |
| 60 | (acetate)2 | dichloride | 1 | 95.9 | 11.0 |
| 61 | (HF-acac)2 | dibromide | 1 | 100 | 100 |
| 62 | (HF-acac)2 | dibromide | 1 | 100 | 100 |
| 63 | (acac)2 | dibromide | 1 | 100 | 100 |
| 64 | (acac)2 | dibromide | 1 | 100 | 100 |
| 65 | (acac)3 | dibromide | 1 | 100 | 100 |
| 66 | (acac)3 | dibromide | 1 | 100 | 100 |
| 67 | dichloride | dibromide | 1 | 100 | 100 |
| 68 | dichloride | dibromide | 1 | 100 | 100 |
| 69 | dibromide | dibromide | 1 | 100 | 100 |
| 70 | dibromide | dibromide | 1 | 100 | 100 |
| 71 | (acetate)3 | dibromide | 1 | 100 | 100 |
| 72 | (acetate)3 | dibromide | 1 | 100 | 100 |
| 73* | (picolinate)2 | dibromide | none | 100 | 50.1 |
| 74* | (picolinate)3 | dibromide | none | 100 | 22.9 |
| 75* | Br(acac)2 | dibromide | none | 100 | 100 |
| 76* | none | dibromide + (picolinate)2 | none | 100 | 34.2 |

*sample taken at 60 minutes

EXAMPLES 77–83

Oxidation reactions were performed at 150° C. and 3447 kilopascals using 28% oxygen-enriched air and 2 molar 4ClOX in glacial acetic acid in the presence of 0.5 mole % cobalt source or of manganese source or of each, both based on ortho-chloro-xylene. Various promoters were included in the reaction mixture at 0.5 mole % based on ortho-chloro-xylene. The promoters used were tetraethylammonium bromide, tetrabutylammonium bromide, and sodium bromide. Temperature and pressure were controlled to remain relatively constant throughout the reaction. The reactions were run for 60 minutes before sampling. Analytical results are shown in Table 3.

TABLE 3

| Example | Manganese source | Cobalt source | Promoter | 4ClOX Conversion | % Yield Diacid |
|---|---|---|---|---|---|
| 77 | (acetate)3 | (acetate)2 | none | 0 | 0 |
| 78 | (acetate)3 | none | NaBr | 6.7 | 0 |
| 79 | (acetate)3 | (acetate)2 | NaBr | 100 | 100 |
| 80 | (acetate)3 | none | TEAB | 12.4 | 0 |
| 81 | (acetate)3 | (acetate)2 | TEAB | 100 | 87.6 |

TABLE 3-continued

| Example | Manganese source | Cobalt source | Promoter | 4ClOX Conversion | % Yield Diacid |
|---|---|---|---|---|---|
| 82 | (acetate)3 | none | TBAB | 10.6 | 0 |
| 83 | (acetate)3 | (acetate)2 | TBAB | 100 | 95.5 |

EXAMPLES 84–93

Oxidation reactions were performed at 150° C. and 3447 kilopascals using 28% oxygen-enriched air and 2 molar 4ClOX in glacial acetic acid in the presence of 0.5 mole % cobalt source or of manganese source or of each, both based on ortho-chloro-xylene. A third metal compound was included in the reaction mixture at 0.5 mole % based on ortho-chloro-xylene. The third metal compounds used were iron (II) bromide, iron (II) chloride, manganese (II) bromide, manganese (II) chloride, cobalt (II) chloride, cobalt (II) bromide, copper (I) bromide, and copper (II) bromide. Temperature and pressure were controlled to remain relatively constant throughout the reaction. The reactions were run for 60 minutes before sampling. Promoters and analytical results are shown in Table 4.

TABLE 4

| Example | Manganese source | Cobalt source | 3d metal compound | 4ClOX Conversion | % Yield Diacid |
|---|---|---|---|---|---|
| 84 | (acetate)3 | none | FeBr2 | 11.5 | 0 |
| 85 | (acetate)3 | none | MnBr2 | 26.5 | 0 |
| 86 | (acetate)3 | (acetate)2 | FeCl2 | 14.9 | 0 |
| 87 | (acetate)3 | (acetate)2 | MnBr2 | 100 | 95.0 |
| 88 | (acetate)3 | (acetate)2 | MnCl2 | 42.0 | 0 |
| 89 | (acetate)3 | (acetate)2 | FeBr2 | 100 | 64.6 |
| 90 | (acetate)3 | (acetate)2 | CoCl2 | 84.1 | 6.9 |
| 91 | (acetate)3 | (acetate)2 | CoBr2 | 100 | 100 |
| 92 | (acetate)3 | (acetate)2 | CuBr | 89.2 | 9.1 |
| 93 | (acetate)3 | (acetate)2 | CuBr2 | 81.6 | 6.2 |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for oxidizing a substrate comprising at least one halo-ortho-xylene which comprises combining the substrate in a solvent with at least one metal catalyst and heating in the presence of an oxygen source to produce a product comprising halo-ortho-phthalic acid or halo-ortho-phthalic anhydride.

2. The method of claim 1 wherein the substrate comprises chloro-ortho-xylene or fluoro-ortho-xylene.

3. The method of claim 1 wherein the substrate further comprises at least one halo-toluic acid.

4. The method of claim 3 wherein the halo-toluic acid comprises at least one chlorotoluic acid.

5. The method of claim 1 wherein the solvent comprises acetic acid.

6. The method of claim 1 wherein the at least one metal catalyst comprises at least one compound of cobalt.

7. The method of claim 6 wherein the at least one metal catalyst further comprises at least one metal compound containing a metal selected from the group consisting of manganese, iron, copper, vanadium, and molybdenum.

8. The method of claim 7 in which the molar ratio of halo-ortho-xylene substrate to the at least one metal catalyst is in a range of about 20–600:1.

9. The method of claim 6 wherein the reaction mixture further comprises an effective amount of at least one promoter selected from the group consisting of (i) phthalimide, 4-chloro-phthalimide, 3-chloro-phthalimide, dichloro-phthalimide, N-hydroxyethylphthalimide, N-hydroxymethylphthalimide;

(ii) N-hydroxyphthalimide, 4-chloro-N-hydroxyphthalimide, 3-chloro-N-hydroxyphthalimide, dichloro-N-hydroxyphthalimide, 4-bromo-N-hydroxyphthalimide, 3-bromo-N-hydroxyphthalimide, dibromo-N-hydroxyphthalimide, N-hydroxymaleimide, N-hydroxysuccinimide;

(iii) 2-carboxyethanehydroxamic acid, 2-carboxyethenehydroxamic acid, 2-carboxyphenylhydroxamic acids of formula I:

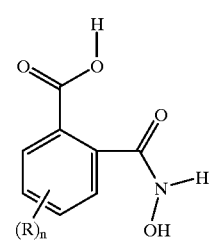

(I)

wherein each R is independently halogen, chloro or bromo; or alkyl, and n is 0–4;

(iv) substituted benzaldehydes of the formula (II):

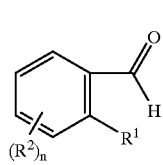

(II)

wherein $R^1$ is alkyl and each $R^2$ is independently halogen, chloro or bromo; or alkyl, and n is 0–4;

(v) ammonium halides, ammonium chlorides, ammonium bromides, phosphonium halides, phosphonium chlorides, phosphonium bromides;

(vi) guanidinium halides, guanidinium chlorides, guanidinium bromides; and (vii) alkali metal halides, alkali metal chlorides, and alkali metal bromides.

10. The method of claim 1 in which the reaction mixture is heated to a temperature in a range of between about 100° C. and about 230° C. at pressure in a range of between about 1300 and about 8300 kilopascals.

11. The method of claim 1 wherein the product mixture comprises halo-phthalic acid or halo-phthalic anhydride.

12. A method for oxidizing a substrate comprising 4-chloro-ortho-xylene which comprises combining chloro-ortho-xylene in acetic acid solvent with at least one metal catalyst which is a metal compound comprising cobalt, and heating in the presence of an oxygen source to produce a product comprising 4-chlorophthalic acid or 4-chlorophthalic anhydride.

13. The method of claim 12 wherein the substrate further comprises 3-chloro-ortho-xylene.

14. The method of claim 12 wherein the substrate further comprises chlorotoluic acid.

15. The method of claim 12 wherein the substrate further comprises both 3-chloro-ortho-xylene and chlorotoluic acid.

16. The method of claim 12 wherein the at least one metal catalyst further comprises at least one metal compound containing a metal selected from the group consisting of manganese, iron, and copper.

17. The method of claim 12 in which the molar ratio of 4-chloro-ortho-xylene substrate to the at least one metal catalyst is in a range of about 50–300:1.

18. The method of claim 12 wherein the reaction mixture further comprises an effective amount of at least one promoter selected from the group consisting of
   (i) phthalimide, 4-chloro-phthalimide, 3-chloro-phthalimide, dichloro-phthalimide;
   (ii) N-hydroxyphthalimide, 4-chloro-N-hydroxyphthalimide, 3-chloro-N-hydroxyphthalimide, dichloro-N-hydroxyphthalimide, 4-bromo-N-hydroxyphthalimide, 3-bromo-N-hydroxyphthalimide, dibromo-N-hydroxyphthalimide, N-hydroxymaleimide, N-hydroxysuccinimide;
   (iii) 2-carboxyphenylhydroxamic acids of formula I:

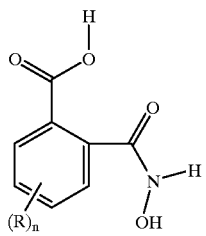

(I)

wherein each R is independently halogen, chloro or bromo; or alkyl, and n is 0–4;

(iv) substituted benzaldehydes of the formula (II):

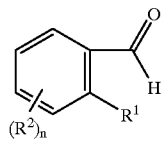

(II)

wherein $R^1$ is alkyl and each $R^2$ is independently halogen, chloro or bromo; or alkyl, and n is 0–4;

(v) ammonium halides, ammonium chlorides, ammonium bromides, (vii) alkali metal halides, alkali metal chlorides, and alkali metal bromides.

19. The method of claim 12 in which the reaction mixture is heated to a temperature in a range of between about 100° C. and about 230° C. at pressure in a range of between about 1300 and about 8300 kilopascals.

20. A method for producing a product mixture comprising 4-chlorophthalic acid or 4-chlorophthalic anhydride which comprises oxidizing a substrate comprising 4-chloro-ortho-xylene, optionally in the presence of chlorotoluic acid, which comprises the steps of
   (i) combining substrate in acetic acid solvent with at least one metal catalyst comprising cobalt, and optionally manganese, and heating in the presence of an oxygen source to a temperature in a range of between about 100° C. and about 230° C. at pressure in a range of between about 1300 and about 8300 kilopascals, wherein the molar ratio of substrate to the at least one metal catalyst is in a range of about 80–250:1; and
   (ii) isolating product comprising 4-chlorophthalic acid or 4-chlorophthalic anhydride.

21. The method of claim 20 wherein the substrate further comprises 3-chloro-ortho-xylene.

22. The method of claim 20 wherein the reaction mixture further comprises an effective amount of at least one promoter selected from the group consisting of N-hydroxyphthalimide, 4-chloro-N-hydroxyphthalimide, 3-chloro-N-hydroxy-phthalimide, N-hydroxymaleimide, N-hydroxysuccinimide, 2-carboxyphenylhydroxamic acid, 4-chloro-2-methylbenzaldehyde, tetraethylammonium bromide, tetrabutylammonium bromide, and sodium bromide.

* * * * *